United States Patent
Urayama et al.

(10) Patent No.: US 8,790,425 B2
(45) Date of Patent: Jul. 29, 2014

(54) METHOD FOR AGGREGATING AND SEPARATING ALGAE

(75) Inventors: Hiroshi Urayama, Nagoya (JP); Minoru Kurata, Nagoya (JP); Hiroaki Fukuda, Obu (JP)

(73) Assignee: Toyota Jidosha Kabushiki Kaisha, Aichi-ken (JP)

( * ) Notice: Subject to any disclaimer, the term of this patent is extended or adjusted under 35 U.S.C. 154(b) by 501 days.

(21) Appl. No.: 13/071,719

(22) Filed: Mar. 25, 2011

(65) Prior Publication Data

US 2011/0239531 A1  Oct. 6, 2011

(30) Foreign Application Priority Data

Apr. 1, 2010  (JP) ................................. 2010-085228

(51) Int. Cl.
*C10L 1/18* (2006.01)
*B01D 21/01* (2006.01)

(52) U.S. Cl.
USPC ............................................. 44/385; 210/724

(58) Field of Classification Search
USPC ............................... 435/134; 44/385; 210/724
See application file for complete search history.

(56) References Cited

U.S. PATENT DOCUMENTS

| | | | |
|---|---|---|---|
| 5,853,598 A * | 12/1998 | Ogoshi et al. | 210/724 |
| 2008/0220486 A1* | 9/2008 | Weiss | 435/134 |
| 2009/0215140 A1 | 8/2009 | Kurano et al. | |
| 2010/0077654 A1* | 4/2010 | Wu et al. | 44/385 |

FOREIGN PATENT DOCUMENTS

| | | |
|---|---|---|
| JP | 06-182356 A | 7/1994 |
| JP | 08-173999 A | 7/1996 |
| WO | 2007/025145 A2 | 3/2007 |

* cited by examiner

*Primary Examiner* — Prem C Singh
*Assistant Examiner* — Chantel Graham
(74) *Attorney, Agent, or Firm* — Sughrue Mion, PLLC

(57) ABSTRACT

The object of the present invention is to provide a method for aggregating and separating algae dispersed in a liquid efficiently.
According to the present invention, a method for aggregating and separating algae dispersed in a liquid, which comprises adding an alkaline inorganic aggregating agent to the liquid at pH of 2.0 to 4.0 in which algae are dispersed, followed by adding a cationic polymer aggregating agent, is provided. Further, according to the present invention, a method for producing biofuel utilizing algae is provided.

9 Claims, 1 Drawing Sheet

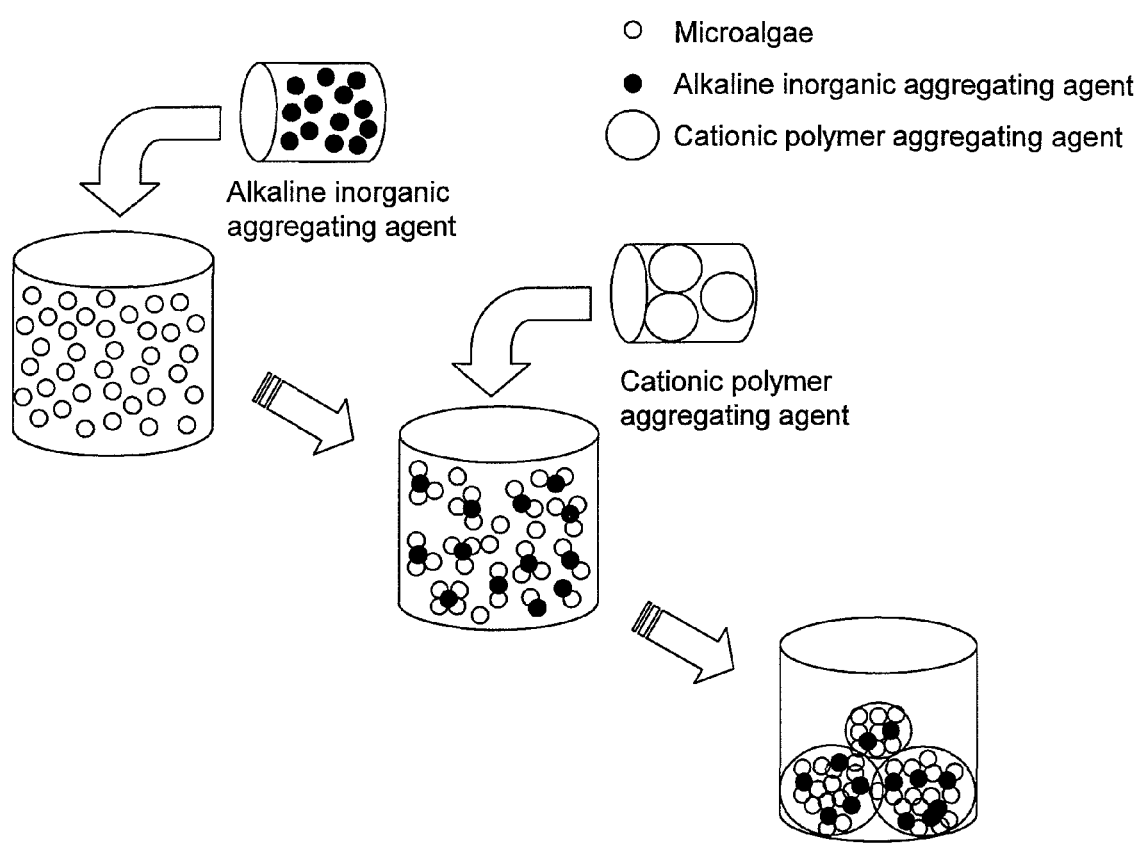

METHOD FOR AGGREGATING AND SEPARATING ALGAE

BACKGROUND OF THE INVENTION

1. Field of the Invention

The present invention relates to a technology of biofuel production, particularly to a technology for collecting algae efficiently in the biofuel production utilizing algae.

2. Background Art

Biofuels have attracted attention as an alternative to fossil fuels which are considered to be depleted such as petroleum. The biofuels are fuels produced using bioresources such as plants as raw materials. The representative examples of biofuels include bioethanol obtained by alcoholic fermentation of sugars derived from corns and sugarcanes, and biodiesel obtained by modifying oils and fats such as vegetable oil. However, it is problematic to secure raw materials in the production of conventional biofuels. In particular, since the raw materials for bioethanol are also food, the growth of bioethanol production has caused an increase in food and feed prices and become a major social issue. Therefore, it has been searched for methods of biofuel production which have little effect on food supply.

As new raw materials of biofuels, microalgae, which have a property of producing oils and fats through photosynthesis and store them, have attracted attention. Biofuel production using microalgae has such advantages that it does not compete with food production, productivity per unit area is higher than that of plants, even lands unsuitable for plant cultivation can be utilized, and a contribution rate for carbon dioxide fixation is high. For example, WO 2007/025145 A discloses a method for producing biodiesel by cultivating algae in a bioreactor and extracting oil therefrom.

Cultivated microalgae usually exist in a dispersed form in a culture medium. Therefore, it is necessary to separate the microalgae from the culture medium for efficient extraction of oils and fats from microalgae. For example, WO 2007/025145 A proposes a process for separating algae by adding an aggregating agent, such as clay, aluminum sulfate, or polyacrylamide.

As to methods for collecting algae dispersed in a liquid, a variety of approaches have been taken, for example, in the field of sewage disposal. For example, JP Patent Publication (Kokai) No. 6-182356 A (1994) discloses a method for processing water containing algae by using a mixture of polyaluminum chloride and poly(dimethyldiallylammonium chloride). Also, JP Patent Publication (Kokai) No. 8-173999 A (1996) discloses a method for aggregating sludge by adding a poly(ferric sulfate) aggregating agent to a mixed sludge and further adding polyamidine after adjusting pH of the resultant to 4 to 7.

SUMMARY OF THE INVENTION

However, the algae separation efficiency by the method described in WO 2007/025145 A is not yet satisfactory with the view of industrialization. Further, the methods using polyaluminum chloride and poly(ferric sulfate) described in JP Patent Publication (Kokai) No. 6-182356 A (1994) and JP Patent Publication (Kokai) No. 8-173999 A (1996) are unable to aggregate algae when the algae are cultivated in acidic environment. Further, the use of polyamidine is not preferable because it increases cost. Thus, the technique for separating algae from a culture efficiently has been demanded. Accordingly it is an object of the present invention to provide a method for aggregating and separating algae dispersed in a liquid efficiently.

We have studied aggregating agents for aggregating algae and found that algae are aggregated and separated rapidly by adding an alkaline inorganic aggregating agent followed by adding a cationic polymer aggregating agent. The gist of the present invention is as flows.

(1) A method for aggregating and separating algae dispersed in a liquid, which comprises adding an alkaline inorganic aggregating agent to the liquid at pH 2.0 to 4.0 in which the algae are dispersed, followed by adding a cationic polymer aggregating agent.

(2) The method according to (1), wherein the alkaline inorganic aggregating agent is sodium aluminate, potassium aluminate, Portland cement, or a mixture of two or more thereof.

(3) The method according to (1) or (2), wherein the cationic polymer aggregating agent is a homopolymer of a cationic monomer, a copolymer of a cationic monomer and a nonionic monomer, a condensed polyamine, polyvinylamine, polyvinylamidine, poly(meth)allylamine, dicyandiamide-formalin condensate, polyethyleneimine, polyvinylimidaline, polyvinylpyridine, diallylamine salt-sulfur dioxide copolymer, a poly(dimethyldiallylammonium salt)-sulfur dioxide copolymer, poly(dimethyldiallylammonium salt), a poly(dimethyldiallylammonium salt)-acrylamide copolymer, an allylamine salt polymer, or a mixture of two or more thereof.

(4) The method according to any one of (1) to (3), wherein the algae are those of Chlorophyta or Rhodophyta.

(5) A method for producing biofuel, which comprises: preparing a liquid in which algae of Chlorophyta or Rhodophyta are dispersed; aggregating and separating the algae by the method according to any one of (1) to (3); and collecting the algae from the liquid to extract oils and fats contained.

According to the method of aggregation and separation of the present invention, it is possible to collect algae dispersed in a liquid efficiently. Also, according to the method of aggregation and separation of the present invention, the efficiency of collecting algae that produce oils and fats from a culture medium can be increased, thereby contributing to the practical application of biofuel production utilizing algae. According to the method of the present invention, an industrializable method of biofuel production utilizing algae can be provided.

This specification incorporates the content of the specification of Japanese Patent Application No. 2010-085228, for which priority is claimed to the present application.

BRIEF DESCRIPTION OF THE DRAWING

FIG. 1 schematically shows the method of the present invention.

DETAILED DESCRIPTION OF THE PREFERRED EMBODIMENTS

The present invention relates to a method for aggregating and separating algae dispersed in a liquid. The term "algae" as used herein refers to all that generally called algae (e.g., green algae, red algae, dinoflagellatae, blue-green algae, and the like) live in water (freshwater or seawater). The method of the present invention is superior in aggregation and separation of microalgae belonging to Chlorophyta or Rhodophyta dispersed in water. In particular, the method of the present invention is suitable for aggregating and separating microalgae having a property of producing oils and fats through photosynthesis and store them. Examples of such microalgae include algae of *Pseudochoricystis* sp. including *Pseudochoricystis ellipsoidea, Choricystis* sp., *Chlamydomonas* sp. including *Chlamydomonas reinhardtii, Cyanidioschyzon* sp. including *Cyanidioschyzon merolae*, and *Cyanidium* sp. including *Cyanidium caldarium.*

*Pseudochoricystis ellipsoidea* is a freshwater green alga having an oval or slightly bended kidney shaped and a cell length of 3 to 4 µm. This alga has a property to grow fast while inorganic nutrition (nitric acid, phosphoric acid, potassium and the like) is rich, whereas it absorbs water and carbon dioxide through photosynthesis and stores a huge amount of oils and fats within the cells when the nutrition is depleted. The stored oils and fats are saturated or unsaturated aliphatic hydrocarbons having 10 to 25 carbon atoms, and equivalent to light oil.

*Chlamydomonas* is a unicellular flagellate belonging to Chlorophyceae, particularly, *Chlamydomonas reinhardtii* belonging to *Chlamydomonas* is widely known as a model organism in the field of molecular biology and the like. The appearance of the cell is smooth oval and the length is about 10 to 20 µm.

*Cyanidioschyzon* and *Cyanidium caldarium* are algae belonging to Rhodophyceae, and known as hot spring algae living near the source of hot springs and in a bathtub. The diameter of *Cyanidioschyzon* cells is about 1 to 2 µm. Cells of *Cyanidium caldarium* are round and have a diameter of a few µm to tens of µm.

In the method of the present invention, an alkaline inorganic aggregating agent is firstly added to a liquid in which algae are dispersed. The liquid as dispersion medium is, but not particularly limited to, for example, water, or culture media for algae containing one or more of the following substances in the water: nutrient salts (nitrogen source such as $NaNO_3$, $KNO_3$, $NH_4Cl$, and urea, or phosphorus source such as $K_2HPO_4$, $KH_2PO_4$, and sodium glycerophosphate), trace amount of metal salts (such as iron, magnesium, manganese, calcium, and zinc), vitamins (such as vitamin B1, and vitamin B12). In the method of the present invention, the pH range of the liquid containing dispersed algae is from 2.0 to 4.0, preferably from 2.5 to 3.5. According to the method of the present invention, it is possible to aggregate and separate algae dispersed in an acidic liquid. In the method of the present invention, the concentration of algae in the liquid is preferably from 0.1 to 3.0 g/L, particularly from 0.3 to 1.0 g/L, based on the dry weight of algae. When the concentration of algae is high, the concentration can be adjusted by dilution with water to the above concentration.

Examples of the alkaline inorganic aggregating agents which can be used in the method of the present invention include sodium aluminate, potassium aluminate, and Portland cement. Among these, sodium aluminate is particularly preferable as an alkaline inorganic aggregating agent. Two or more alkaline inorganic aggregating agents can be mixed for use. In the method of the present invention, an addition amount of the alkaline inorganic aggregating agents is preferably 0.6% by weight or more with respect to the dry weight of whole algae contained in the liquid. Also, an addition amount of the alkaline inorganic aggregating agents is preferably 0.6 to 30.0% by weight with respect to the dry weight of the whole algae contained in the liquid, more preferably 0.6 to 20.0% by weight, further preferably 0.6 to 10.0% by weight, specifically 0.6 to 4.5% by weight, particularly 0.6 to 3.0% by weight.

When an alkaline inorganic aggregating agent is added to a liquid containing dispersed algae, the algae and the inorganic aggregating agent are bonded to form flocs. However, the size of flocs formed here is not enough to sediment the algae, and small flocs of the algae dispersed in the liquid are observed at this time.

Then, a cationic polymer aggregating agent is added thereto. Examples of the cationic polymer aggregating agents which can be used in the method of the present invention include a homopolymer of a cationic monomer, a copolymer of a cationic monomer and a nonionic monomer, condensed polyamine, polyvinylamine, polyvinylamidine, poly(meth)allylamine, dicyandiamide-formalin condensate, polyethyleneimine, polyvinylimidaline, polyvinylpyridine, a diallylamine salt-sulfur dioxide copolymer, a poly(dimethyldiallylammonium salt)-sulfur dioxide copolymer, poly(dimethyldiallylammonium salt), a polydimethyldiallylammonium salt-acrylamide copolymer, and an allylamine salt polymer. As the cationic polymer aggregating agents which can be used in the method of the present invention, particularly preference is given to the homopolymer of a cationic monomer and the copolymer of a cationic monomer and a nonionic monomer.

In the homopolymer of a cationic monomer or the copolymer of a cationic monomer and a nonionic monomer, examples of the cationic monomer include alkylaminoalkyl methacrylate including dimethylaminoethyl methacrylate, dialkylaminoalkyl acrylate including dimethylaminoethyl acrylate and diethylaminoethyl acrylate, and a neutralized salt or quaternary salt thereof. On the other hand, examples of the nonionic monomers include acrylamide, methacrylamide, methacrylonitrile, and vinylacetate. As used herein, alkyl denotes $C_{1-6}$ alkyl (such as methyl, ethyl, n-propyl, isopropyl, n-butyl, isobutyl, t-butyl, pentyl, and hexyl), $C_{2-6}$ alkenyl (such as vinyl, 1-propenyl, 2-propenyl, 1-butenyl, 2-butenyl, 3-butenyl, 1-methyl-2-propenyl, 1-pentenyl, 2-pentenyl, 3-pentenyl, 4-pentenyl, 1-methyl-2-butenyl, 2-methyl-3-butenyl, 1-hexenyl, 2-hexenyl, 3-hexenyl, 4-hexenyl, 5-hexenyl, 1,1-dimethyl-2-butenyl, and 2-methyl-3-pentenyl) or $C_{2-6}$ alkynyl (such as ethynyl, 1-propynyl, 2-propynyl, 1-butyryl, 2-butyryl, 3-butyryl, 1-methyl-2-propynyl, 1-pentynyl, 2-pentynyl, 3-pentynyl, 4-pentynyl, 1-methyl-2-butyryl, 1-hexynyl, 2-hexynyl, 3-hexynyl, 4-hexynyl, 5-hexynyl, 1,1-dimethyl-2-butyryl, and 2-methyl-3-pentynyl).

Among these, poly(dialkylaminoalkyl methacrylate) (particularly, poly(dimethylaminoethyl methacrylate)) and acrylamide-dialkylaminoalkyl acrylate copolymer (particularly, acrylamide-dimethylaminoethyl acrylate copolymer) are preferred as cationic polymer aggregating agents. Two or more of cationic polymer aggregating agents can be mixed for use.

When a cationic polymer aggregating agent is added to the above liquid to which an alkaline inorganic aggregating agent is added in advance, the flocs formed by bonding of the algae and the inorganic aggregating agent are entangled by the polymer aggregating agent to form larger flocs. Since the size of these flocs is too large to be maintained in the dispersed state in water, they easily sediment.

In the method of the present invention, the addition concentration of cationic polymer aggregating agents can be determined arbitrarily. For example, a cationic polymer aggregating agent can be added appropriately while visually observing the process that relatively small algae flocs formed by addition of an alkaline inorganic aggregating agent grow to large flocs and settle out as the cationic polymer aggregating agent is added. The concentration of the cationic polymer aggregating agent is generally preferably 0.01 to 0.5% by weight with respect to the dry weight of the whole algae contained in the liquid, specifically 0.01 to 0.3% by weight, particularly 0.05 to 0.25% by weight.

FIG. 1 schematically shows the method of the present invention. As explained above, the method of the present invention is a method in which firstly an alkaline inorganic aggregating agent is added to a liquid containing dispersed algae, and secondly a cationic polymer aggregating agent is added thereto. When an alkaline inorganic aggregating agent is added to a liquid containing dispersed algae, flocs of a relatively small size are formed. However, since these small flocs are not enough for the algae to sediment, they are still in a dispersed state in the liquid. When a cationic polymer aggregating agent is added thereto, the above small flocs are entangled by the polymer aggregating agent to form larger flocs. Since the size of these flocs at this stage is too large to be maintained in the dispersed state in water, they easily sediment.

In another aspect, the present invention relates to a method for producing biofuel. In the method for producing biofuel of the present invention, first, a liquid in which algae having a property of producing oils and fats and store them are dispersed is prepared. Examples of those algae include the above mentioned algae belonging to Chlorophyta or Rhodophyta. The liquid in which algae are dispersed can be obtained, for example, by cultivating those algae artificially using a bioreactor as a closed system, or by cultivating in an open pond as an open system. As regards algae belonging to *Pseudochoricystis* or *Choricystis*, particularly for *Pseudochoricystis ellipsoidea*, see WO 2006/109588, for example.

Then, according to the above mentioned method of aggregation and separation, an alkaline inorganic aggregating agent is added to the prepared liquid containing dispersed algae, and thereafter a cationic polymer aggregating agent is added. This makes the algae to aggregate to form flocs and to settle out. The sedimented algae flocs can be separated from the liquid, for example, by filtration.

Lastly, the oils and fats being stored within algae are extracted from the collected algae flocs. The extraction of oils and fats can be conducted by general methods for those skilled in the art, for example, (1) a method of destroying cells by a French press, a homogenizer or the like, then extracting oils and fats with an organic solvent such as n-hexane, (2) a method of collecting cells on a filter made of glass fiber or the like, and drying it, then extracting oils and fats with an organic solvent, (3) a method of freezing and drying cells to powderize and extracting oils and fats from the powder with an organic solvent, (4) a method of dewatering algae by a filter press or a screw press, and extracting oils and fats with an organic solvent, and (5) a method of extracting oils and fats with a supercritical fluid or subcritical fluid of water, carbon dioxide, methanol and the like, instead of organic solvents.

For example, oils and fats which can be extracted from algae belonging to *Pseudochoricystis* or *Choricystis*, particularly *Pseudochoricystis ellipsoidea* are saturated or unsaturated aliphatic hydrocarbons having 10 to 25 carbon atoms, and equivalent to light oil. The aliphatic hydrocarbons can be obtained in an amount of up to about 30% of dry weight of the above mentioned algae. The residue after the extraction can also be used as a raw material for bioethanol fuel production.

EXAMPLES

Hereinafter, the present invention will be described in detail by referring to examples, however, the present invention is not limited to these Examples.

Reference Examples 1 to 6

The aggregation ability of each of inorganic aggregating agents was evaluated when they were used alone. A microalga, *Pseudochoricystis ellipsoidea*, was cultivated in a 500 mL bioreactor. The concentration of the algae in the culture medium during cultivation was 2.5 to 3.0 g/L, and the pH of the culture medium was 3 to 3.5. The culture medium was diluted with distilled water to 0.5 g/L, and after stirring well, 100 mL thereof was taken into a beaker. To the beaker, a stirrer chip (φ7×20 (mm)) was added, and with stirring by a multi-stirrer (AS ONE corporation) (the stirring rate was at 5 out of 10 scale), a predetermined amount of an inorganic aggregating agent was added. And sodium aluminate, which is in powder form, was dissolved in distilled water in advance and added as 5% by weight aqueous solution. The details of the used inorganic aggregating agents are as shown in Table 1. The addition concentration of the aggregating agent was determined as % by weight with respect to dried algae body by dividing the addition amount of the aggregating agent (g) by the weight of algae (g) contained in the system (as dried algae body).

TABLE 1

| Inorganic Aggregating Agent | Trade Name (Supplier) | Acidity/ Alkalinity | Property |
|---|---|---|---|
| Sodium Aluminate $NaAlO_2$ | NAP-120 (Asahi Chemical) | Strong Alkaline | White Powder |
| Polyaluminum Chloride $[Al_2(OH)_nCl_{6-n}]_m$ ($1 \le n \le 5$, $m \le 10$) | PAC (Asahi Chemical) | Mild Acidic (pH = 4.2) | Transparent Liquid |
| Poly(ferric sulfate) $[Fe_2(OH)_n(SO_4)_{3-n/2}]_m$ ($0 < n \le 2$ m) | Polytetsu (Nittetsu Mining) | Strong Acidic (pH > 2) | Brown Liquid |

Evaluation of Sedimentation

After addition of an aggregating agent, the liquid containing algae was stirred for 5 minutes, and transferred to a 100 mL graduated cylinder promptly. After standing for 10 minutes, the height of sedimented flocs (agglomerate) was measured with the scale of the graduated cylinder. The value (mL), read off from the graduated cylinder, was divided by the concentration of algae (0.5 g/L), and the obtained value was used as an index to evaluate the sedimentation. The evaluation standard was A: $10 \le X$, B: $5 \le X < 10$, C: $2 \le X < 5$, D: $0 \le X < 2$ when the obtained value was X.

Evaluation of Aggregation

As in the case of the above, after addition of an aggregating agent, the liquid containing the algae was stirred further for 5 minutes, and transferred to a 100 mL graduated cylinder promptly. After standing for 10 minutes, 20 mL of the supernatant was sampled by pipette from the position of 70 mL mark on the graduated cylinder. The sampled supernatant was separated by suction filtration using a glass fiber filter paper GF/F (4.7 cm). The filter paper was dried at 105° C. for 3 hours, and the dry weight of the algae contained in the supernatant was measured. The supernatant residue was obtained as % by weight by dividing the weight of the algae in the supernatant (g) by the weight of algae (g) contained in the system before aggregation (the weight of algae is as dried algae body). The evaluation standard was A: $0 \le Y < 3$, B: $3 \le Y < 10$, C: $10 \le Y < 50$, D: $50 \le Y$ when the supernatant residue (%) was Y.

pH Measurement of Solution

The pH values of the liquid were measured by a pH measuring device (pH METER F-22, HORIBA) at the time before an aggregating agent is added and after flocs are sedimented and separated by adding the aggregating agent.

The results of Reference Examples 1 to 6 are shown in Table 2.

TABLE 2

|  | Reference Ex. 1 | Reference Ex. 2 | Reference Ex. 3 | Reference Ex. 4 | Reference Ex. 5 | Reference Ex. 6 |
|---|---|---|---|---|---|---|
| Inorganic Aggregating Agent | Sodium Aluminate (5% by weight aqueous solution) | | | | Polyaluminum Chloride | Poly(ferric sulfate) |
| Type of Aggregating Agent | Alkaline | | | | Acidic | Acidic |
| Addition Amount of Aggregating Agent (μL) | 20 | 25 | 50 | 100 | 50 | 50 |
| Addition Concentration of Aggregating Agent (% by weight for dried algae body) | 2 | 2.5 | 5 | 10 | — | — |
| Sedimentation Index Value | 6 | 6 | 0 | 0 | 0 | 0 |
| Evaluation | B | B | D | D | D | D |
| Aggregation Supernatant Residue (% by weight) | 53.7 | 46.8 | — | — | — | — |
| Evaluation | D | C | — | — | — | — |
| pH Before Addition | 3.7 | 3.7 | 3.7 | 3.7 | — | — |
| After Addition | 7 | 7.8 | 8.7 | 9.1 | — | — |

In Reference Examples 5 and 6, in which polyaluminum chloride or poly(ferric sulfate) (acidic) was used as an inorganic aggregating agent, aggregation of algae hardly occurred even though various different addition concentrations of the aggregating agent are used. On the other hand, in the Reference Example 1 or 2, in which sodium aluminate was added at 2% by weight or 2.5% by weight of addition concentration, aggregation of algae was observed. However, flocs of large size were not observed, and the aggregation ability thereof was considered as being insufficient. The aggregation and size of flocs were not improved even though the concentration of sodium aluminate was 5% by weight or more, or 0.5% by weight or less.

Reference Examples 7 to 15

The aggregation ability was evaluated when each of polymer aggregating agents was used alone. As in the case of the Reference Examples 1 to 6, 100 mL of the liquid containing of microalgae *Pseudochoricystis ellipsoidea* at a 0.5 g/L concentration was taken into a beaker. With stirring by a multi stirrer, an amount of a predetermined polymer aggregating agent was added as 0.2% by weight aqueous solution prepared by dissolving in distilled water. The details of the used polymer aggregating agents are shown in the Table 3.

TABLE 3

| Polymer Aggregating Agent | Trade Name (Supplier) | Ionicity | Property |
|---|---|---|---|
| Poly(dimethylaminoethyl methacrylate) $[CH_2C(CH_3)COO(CH_2)_2N(CH_3)_2]_n$ | Kurifarm PC-892 (Kurita Water Industries) | Strong Cationic | White Particles |
| Acrylamide-Dimethylaminoethyl Acrylate Copolymer $[CH_2CHCONH_2]_n—[CH_2CHCOO(CH_2)_2N(CH_3)_2]_m$ | Kurifarm PC-843 (Kurita Water Industries) | Medium Cationic | White Particles |
| Polyacrylamide $[CH_2CHCONH_2]_n$ | ACCOFLOC N-104 (MT AquaPolymer) | Nonionic | White Particles |

Among the polymer aggregating agents, when a cationic aggregating agent was added, the pH of the liquid was adjusted to around 10 with adding potassium hydroxide (KOH) beforehand.

As in the case of Reference Examples 1 to 6, the sedimentation and aggregation were evaluated, and the pH of the solution was measured for each polymer aggregating agent. The results of Reference Examples 7 to 15 are shown in table 4.

TABLE 4

|  | Reference Ex. 7 | Reference Ex. 8 | Reference Ex. 9 | Reference Ex. 10 |
|---|---|---|---|---|
| Polymer Aggregating Agent | Poly(dimethylaminoethyl methacrylate) (0.2% by weight aqueous solution) | | | |
| Type of Aggregating Agent | Cationic | | | |
| Addition Amount of Aggregating Agent (μL) | 25 | 50 | 250 | 500 |
| Addition Concentration of Aggregating Agent (% by weight for dried algae body) | 0.1 | 0.2 | 1 | 2 |
| Sedimentation Index Value | 0 | 10 | 2 | 0 |
| Evaluation | D | A | C | D |

TABLE 4-continued

| | | | | | |
|---|---|---|---|---|---|
| Aggregation | Supernatant Residue (% by weight) | — | 6.4 | 28.8 | — |
| | Evaluation | — | B | C | — |
| pH | Before Addition | — | 10.3 | 10.3 | — |
| | After Addition | — | 10.1 | 10.1 | — |

| | | Reference Ex. 11 | Reference Ex. 12 | Reference Ex. 13 | Reference Ex. 14 | Reference Ex. 15 |
|---|---|---|---|---|---|---|
| Polymer Aggregating Agent | | Acrylamide-Dimethylaminoethyl Acrylate Copolymer (0.2% by weight aqueous solution) | | | | Polyacrylamide (0.2% by weight aqueous solution) |
| Type of Aggregating Agent | | Cationic | | | | Nonionic |
| Addition Amount of Aggregating Agent (μL) | | 25 | 50 | 250 | 500 | 50 |
| Addition Concentration of Aggregating Agent (% by weight for dried algae body) | | 0.1 | 0.2 | 1 | 2 | 0.2 |
| Sedimentation | Index Value | 0 | 4 | 6 | 0 | 0 |
| | Evaluation | D | C | B | D | D |
| Aggregation | Supernatant Residue (% by weight) | — | 19.2 | 3.1 | — | — |
| | Evaluation | — | C | B | — | — |
| pH | Before Addition | — | 10.3 | 10.5 | — | — |
| | After Addition | — | 10.3 | 10.4 | — | — |

In the Reference Example 15, in which a nonionic polymer aggregating agent was used, aggregation of the algae hardly occurred. On the other hand, when dimethylaminoethyl polymethacrylate or acrylamide-dimethylaminoethyl acrylate copolymer was used at the addition concentrations in a certain range, aggregation of algae was observed. However, flocs in a large size were hardly observed, and the aggregation ability was considered as being insufficient.

Examples 1 to 4

Comparative Example 1

The aggregation ability, when a cationic polymer aggregating agent was added after addition of an alkaline inorganic aggregating agent, was examined. As in the above case of Reference Examples 1 to 15, 100 mL of the liquid containing the microalgae *Pseudochoricystis ellipsoidea* at 0.5 g/L concentration was taken into a beaker, and with stirring by a multi stirrer, sodium aluminate was added as 5% by weight aqueous solution prepared by dissolving in distilled water in advance. After stirring for 5 minutes, dimethylaminoethyl polymethacrylate was added as 0.2% by weight aqueous solution prepared by dissolving in distilled water in advance, and the liquid was further stirred for 5 minutes and transferred to a 100 mL graduated cylinder promptly. As in the case of Reference Examples 1 to 16, the sedimentation and aggregation were evaluated and the pH of the solution was measured for each addition concentrations of the aggregating agent. The results of Comparative Example 1 and Examples 1 to 4 are shown in Table 5.

TABLE 5

| | | Comparative Ex. 1 | Ex. 1 | Ex. 2 | Ex. 3 | Ex. 4 |
|---|---|---|---|---|---|---|
| Inorganic Aggregating Agent | | Sodium Aluminate (5% by weight aqueous solution) | | | | |
| Type of Inorganic Aggregating Agent | | Alkaline | | | | |
| Addition Amount of Inorganic Aggregating Agent (μL) | | 5 | 10 | 20 | 25 | 25 |
| Addition Concentration of Inorganic Flocculant (% by weight with respect to dried algae body) | | 0.5 | 1 | 2 | 2.5 | 2.5 |
| Polymer Aggregating Agent | | Poly(dimethylaminoethyl methacrylate) (0.2% by weight aqueous solution) | | | | |
| Type of Polymer Aggregating Agent | | Cationic | | | | |
| Addition Amount of Polymer Aggregating Agent (μL) | | 50 | 50 | 50 | 25 | 50 |
| Addition Concentration of Polymer Aggregating Agent (% by weight with respect to dried algae body) | | 0.2 | 0.2 | 0.2 | 0.1 | 0.2 |
| Sedimentation | Index Value | 0 | 2 | 10 | 10 | 10 |
| | Evaluation | D | C | A | A | A |
| Aggregation | Supernatant Residue (% by weight) | — | — | 1.2 | — | 5.7 |
| | Evaluation | — | — | A | — | B |
| pH | Before Addition | — | 3.7 | 3.7 | 3.7 | 3.7 |
| | After Addition | — | 5.3 | 6.8 | 7.5 | 7.4 |

In Comparative Example 1, in which the addition concentration of sodium aluminate was 0.5% by weight, aggregation of the algae was not observed. However, in other Examples 1 to 4, aggregation of the algae was observed, and both the aggregation and the size of flocs were superior. In particular, in Examples 1 to 4, in which 1 to 2.5% by weight of sodium aluminate and 0.1 to 0.2% by weight of dimethylaminoethyl polymethacrylate were added, it was obvious that the size of the flocs and rate of aggregation were particularly superior by visual observation.

All references, including any publications, patents or patent applications cited in this specification are hereby incorporated by reference in their entirely.

What is claimed is:

1. A method for aggregating and separating algae dispersed in a liquid, which comprises adding an alkaline inorganic aggregating agent to the liquid at pH 2.0 to 4.0 in which the algae are dispersed, followed by adding a cationic polymer aggregating agent.

2. The method according to claim 1, wherein the alkaline inorganic aggregating agent is sodium aluminate, potassium aluminate, Portland cement, or a mixture of two or more thereof.

3. The method according to claim 1, wherein the cationic polymer aggregating agent is a homopolymer of a cationic monomer, a copolymer of a cationic monomer and a nonionic monomer, condensed polyamine, polyvinylamine, polyvinylamidine, poly(meth)allylamine, dicyandiamide-formalin condensate, polyethyleneimine, polyvinylimidaline, polyvinylpyridine, a diallylamine salt-sulfur dioxide copolymer, a poly(dimethyldiallylammonium salt)-sulfur dioxide copolymer, poly(dimethyldiallylammonium salt), a poly(dimethyldiallylammonium salt)-acrylamide copolymer, an allylamine salt polymer, or a mixture of two or more thereof.

4. The method according to claim 2, wherein the cationic polymer aggregating agent is a homopolymer of a cationic monomer, a copolymer of a cationic monomer and a nonionic monomer, condensed polyamine, polyvinylamine, polyvinylamidine, poly(meth)allylamine, dicyandiamide-formalin condensate, polyethyleneimine, polyvinylimidaline, polyvinylpyridine, a diallylamine salt-sulfur dioxide copolymer, a poly(dimethyldiallylammonium salt)-sulfur dioxide copolymer, poly(dimethyldiallylammonium salt), a poly(dimethyldiallylammonium salt)-acrylamide copolymer, an allylamine salt polymer, or a mixture of two or more thereof.

5. The method according to claim 1, wherein the algae are those belonging to Chlorophyta or Rhodophyta.

6. A method for producing biofuel, which comprises:
preparing a liquid in which algae belonging to Chlorophyta or Rhodophyta are dispersed;
aggregating and separating the algae by the method according to claim 1; and
collecting the algae from the liquid to extract oils and fats contained.

7. A method for producing biofuel, which comprises:
preparing a liquid in which algae belonging to Chlorophyta or Rhodophyta are dispersed;
aggregating and separating the algae by the method according to claim 2; and
collecting the algae from the liquid to extract oils and fats contained.

8. A method for producing biofuel, which comprises:
preparing a liquid in which algae belonging to Chlorophyta or Rhodophyta are dispersed;
aggregating and separating the algae by the method according to claim 3; and
collecting the algae from the liquid to extract oils and fats contained.

9. A method for producing biofuel, which comprises:
preparing a liquid in which algae belonging to Chlorophyta or Rhodophyta are dispersed;
aggregating and separating the algae by the method according to claim 4; and
collecting the algae from the liquid to extract oils and fats contained.

* * * * *